United States Patent [19]

Singh et al.

[11] Patent Number: 4,596,768
[45] Date of Patent: Jun. 24, 1986

[54] ANTIBODIES FOR PENICILLOIC ACID THEIR PREPARATION AND USE

[75] Inventors: Prithipal Singh, Sunnyvale; Danton K. Leung, San Jose; Richard Rodgers, Palo Alto, all of Calif.

[73] Assignee: Syntex (U.S.A.) Inc., Palo Alto, Calif.

[21] Appl. No.: 548,164

[22] Filed: Nov. 2, 1983

[51] Int. Cl.$^4$ .................... G01N 33/53; C07K 15/06; A61K 39/00; C12Q 1/00

[52] U.S. Cl. .......................................... 435/7; 424/88; 435/4; 435/18; 435/28; 435/177; 435/188; 435/805; 435/810; 436/530; 436/543; 436/544; 436/547; 436/810; 436/815; 436/822; 436/823; 530/405; 530/364; 530/388; 530/807

[58] Field of Search ............... 436/530, 543, 544, 547, 436/822, 823, 810, 815; 435/188, 805, 810, 4, 18, 7, 28, 177; 260/112 R, 121, 112 B; 424/88

[56] References Cited

U.S. PATENT DOCUMENTS 4,234,683 11/1980 McMillan .............................. 435/18
4,347,312  8/1982 Brown et al. ........................... 435/7

OTHER PUBLICATIONS

Vunakis et al., *Methods in Enzymology*, vol. 70, "Immunochemical Techniques", 1980, Academic Press, New York, pp. 85–104.

Kitagawa et al., "A New Method for Preparation of an Antiserum to Penicillin and Its Application for Novel Enzyme Immunoassay of Penicillin," J. Biochem., vol. 84, No. 2, (1978) pp. 491–494.

Horiuchi et al. "Int. Arch. Allergy", 28:306–320 (1965).

Yolken et al., "J. of Pediatrics", vol. 97, No. 5, pp. 715–720 (1980).

*Primary Examiner*—Robert J. Warden
*Assistant Examiner*—Patricia Kate White
*Attorney, Agent, or Firm*—Bertram I. Rowland; Theodore J. Leitereg

[57] ABSTRACT

Conjugates of penicilloic acid derivatives and certain poly(amino acids), which are either antigenic or enzymatic, are provided. Antibodies raised against the antigenic poly(amino acids) and the enzyme conjugates are used as reagents in immunoassays. In particular, the compounds of the present invention can be used for measuring the presence of a $\beta$-lactamase in a patient serum sample by adding a known amount of penicillin to the sample and observing the production of penicilloic acid over a fixed period of time.

13 Claims, No Drawings

ANTIBODIES FOR PENICILLOIC ACID THEIR PREPARATION AND USE

BACKGROUND OF THE INVENTION

1. Field of the Invention

Various penicillin compounds, such a benzylpenicillin (penicillin G), ampicillin, and the like, are collectively the most widely used antibiotics today. Penicillins are the treatment of choice for a wide variety of bacterial infections because, among other reasons, they are inexpensive and widely available.

A number of bacterial strains, however, are resistant to penicillin treatment, producing $\beta$-lactamases which inactivate penicillin by hydrolyzing the $\beta$-lactam ring. The resulting hydrolyzed compounds (referred to generally as penicilloic acids) display no antibiotic activity.

It would be desirable to provide an assay for measuring the presence of such $\beta$-lactamases in human sera. The assay would serve to detect bacterial infection by $\beta$-lactamase producing organisms, since mammalian tissues do not normally produce this enzyme. Such an assay would also allow the determination of whether the infection was caused by a penicillin-resistant strain since such strains would tend to elaborate higher levels of $\beta$-lactamase than would sensitive organisms.

Direct immunological measurement of $\beta$-lactamases, however, is problematic since different bacteria produce $\beta$-lactamases which are not immunologically cross-reactive. Because of the convenience of immunoassays in general, it is desirable to devise an immunoassay capable of inferentially measuring the level of $\beta$-lactamases present in human sera.

2. Description of the Prior Art

Yolken, et al. (1980) J. Pediatrics 97:715–720, describe a non-immunological radioisotopic assay which measures the presence of $\beta$-lactamases based on the conversion of penicillin to penicilloic acid. Immunogens to penicillin are described in Wal, et al. (1975) FEBS Letters 57:9–13; Munro, et al. (1978) J. Pharm. Sci. 67:1197–1204; and Horiughi and Shibata (1965) Int. Arch. Allergy 28:306–320. Each of these articles teaches that immunogens may be formed by hydrolyzing the $\beta$-lactam ring of penicillin and conjugating directly to the $\epsilon$-amino groups of lysine in the protein carrier. Kitagawa, et al. (1978) J. Biochem. 84:491–494, couple ampicillin to proteins by acylation of the amino group of ampicillin with a functionalized acid and coupling with the protein after reductive cleavage of the disulfide bonds in the cysteine groups of the protein.

SUMMARY OF THE INVENTION

Protein conjugates of penicilloic acids are provided where the proteins are antigens or enzymes. The antigenic conjugates are used for production of antisera to penicilloic acids, and the antisera together with the enzyme conjugates are used as reagents in sensitive immunoassays for detecting penicilloic acid levels in biological fluids. The antiserum for the penicilloic acids is highly specific and displays only a low level of cross-reactivity with the parent penicillin compounds. The reagents are particularly useful in performing assays for $\beta$-lactamase and penicillin.

DESCRIPTION OF THE SPECIFIC EMBODIMENTS

The present invention provides novel immunoassays for the determination of penicillin, derivatives thereof, and $\beta$-lactamases. The immunoassays rely on reagents which include antigenic and enzyme protein conjugates of penicilloic acids and the antisera prepared from the antigenic conjugates. The term penicilloic acids embrace all penicillin antibiotic derivatives characterized by hydrolysis of the $\beta$-lactam ring. The most common penicilloic acids include benzylpenicilloic acid (derived from benzylpenicillin) and ampicilloic acid (derived from ampicillin). The protein-penicilloic acid conjugates of the present invention are characterized by a linkage at the alpha-amino groups indicated in the formula below.

The compounds of the subject invention will for the most part have the following formula:

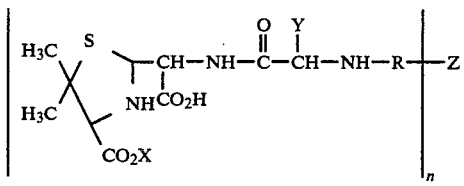

wherein:

X is an alkali metal or hydrogen;

Y is a substituent of a naturally occurring or synthetic penicillin antibiotic usually phenyl;

R is a linking group having from 3 to 9 carbon atoms and from 0 to 5 heteroatoms which are chalcogen (O or S) and nitrogen (N), particularly as amide, usually R will be a straight chain having from 5 to 12 atoms in the chain, more usually having from 7 to 10 atoms in the chain, desirably R will have the formula:

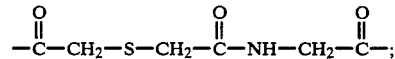

Z is a poly(amino acid) which is an antigen or an enzyme; and n is from 1 to the molecular weight of Z divided by 500, more usually divided by 1,000, and desirably divided by 1,500.

When Z is an antigen, n usually ranges from 1 to 500, typically from 10 to 100; and when Z is an enzyme, n usually ranges from 1 to 30, more usually from 2 to 20, normally being from about 2 to 16.

The molecular weight of the poly(amino acids) will generally be at least about 5,000 and have no upper limit, normally being less than 10,000,000, and usually being not more than about 6,000,000. There will usually be different ranges depending on whether an antigen or an enzyme is involved. With antigens, the range will be from about 5,000 to 10,000,000, usually from about 20,000 to 600,000, and more usually from about 25,000 to 250,000 molecular weight. With enzymes, the range will be from about 10,000 to 600,000, and more usually from about 10,000 to 300,000 molecular weight. For both antigens and enzymes, there will usually be at least about 1 penicilloic acid analog group per 200,000 molecular weight, more usually at least one per 500,000 molecular weight. In the case of intermediate molecular weight antigens (35,000 to 600,000), the number of penicilloic acid analog groups will generally be from about 2 to 250, more usually from 10 to 100. With lower molecular weight antigens, (below 35,000), the number of penicilloic acid analog groups will generally be in the range from about 2 to 10, usually in the range from 2 to 5.

Various protein types may be employed as the antigenic material. These types include albumins, serum proteins, e.g., globulins, ocular lens proteins, lipoproteins, and the like. Illustrative proteins include bovine serum albumin, keyhole limpet hemocyanin, egg ovalbumin, bovine gamma-globulin, and the like. Alternatively, synthetic poly(amino acids) may be prepared having sufficient available amino groups, e.g., lysines.

The enzymes can vary widely, depending on the ease of conjugation, turnover rate, and the physiological fluid in which the penicilloic acid (or related compound) is to be measured. Primarily, the enzymes of choice, based on the I.U.B. classifications are: Class 1, oxidoreductases and Class 3, hydrolases. Particularly in Class 1, the enzymes of interest are dehydrogenases of Class 1.1, more particular, Sub-classes 1.1.1 and 1.1.99 and peroxidases in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Illustrative peroxidases include horseradish peroxidase, and illustrative hydrolases include alkaline phosphatase and glycosidases, e.g., β-galactosidase, β-glucosidase and lysozyme.

The protein conjugates of the present invention can be prepared by acylation of the parent penicillin compound, conjugation of the compound to a protein, and subsequent hydrolysis of the β-lactam ring to yield the penicilloic acid conjugate. For example, methyldithioacetic acid N-hydroxy succinimide ester can be linked through the N-acetyl amino group of ampicillin. The cleavable disulfide bond enables the hapten to be coupled to a protein labelled with bromoacetylglycine N-hydroxy succinimide ester. The resulting penicillin-protein conjugate can be converted to the corresponding penicilloic acid conjugate by hydrolysis of the β-lactam ring under alkaline conditions. This procedure is described in detail in the Examples hereinafter.

By employing the above-described conjugation procedure, the hydrolyzed β-lactam ring provides a distinction between the penicilloic acid and its parent penicillin, resulting in relatively low cross-reactivity between them. The ability to distinguish between penicilloic acid and its corresponding penicillin is critical to the β-lactamase assay described hereinafter which relies on measuring the presence of very low levels of hydrolyzed product (penicilloic acid) in the presence of much greater amounts of the corresponding penicillin.

The immunogen conjugates may be injected into a wide variety of vertebrates in accordance with conventional methods for the production of antibodies. Usually, the animals are bled periodically, with successive bleeds having improved titer and specificity, until reaching a plateau and then diminishing in their specificity and titer. The immunogen conjugates may be injected intramuscularly, intraperitoneally, subcutaneously, or the like. Usually, a vehicle is employed, such as complete or incomplete Freund's adjuvant.

As indicated previously, the antibodies and enzyme reagents prepared in accordance with the subject invention find particular use in immunoassays for the determination of penicillin, penicilloic acids and β-lactamases. The penicillin assay relies on hydrolysing the penicillin and determining the resulting penicilloic acid, while the penicilloic acid assay relies on the direct measurement of penicilloic acid in a physiological sample. Conveniently, the assay may be a homogeneous enzyme immunoassay as described in U.S. Pat. No. 3,817,837. The method involves combining the enzyme conjugate, the sample which contains the penicilloic acids, and an antibody for the penicilloic acid in an aqueous buffered medium at temperatures in the range of from about 10°–50° C., usually of from about 20°–40° C.

Alternatively, a "dipstick assay" can be performed as described in U.S. Pat. No. 4,299,916. The dipstick assay employs a solid support ("dipstick") having the anti-penicilloic acid antisera covalently bound to its surface together with a first enzyme, e.g., glucose oxidase. The dipstick and a second enzyme (e.g., horseradish peroxidase) conjugated to penicilloic acid are incubated in the sample to be tested. The degree of binding between the enzyme conjugate and the immobilized antibody is inversely proportional to the amount of free penicilloic acid in the sample. By adding glucose and an appropriate proto-dye, the glucose oxidase on the dipstick generates hydrogen peroxide, which is utilized by the horseradish peroxidase to convert the proto-dye to an insoluble dye. The insoluble dye remains on the dipstick surface and the degree of color formation is inversely proportional to the presence of penicilloic acid in the sample.

The β-lactamase assay measures the production of penicilloic acid from penicillin over a given period of time. The patient's sample is mixed witth an appropriate buffer and penicillin is added to a final concentration of from about 5–20 μg/ml. The mixture is allowed to incubate, typically for one hour at 37° C., after which time the sample is immediately brought to room temperature to inhibit further enzyme activity. The concentration of penicilloic acid in the mixture may then be measured by either of the techniques described above, and the amount of β-lactamase is determined based on a standard curve. The enzyme activity of various β-lactamases produced by different bacterial strains is generally in the range from about $10^3$ to $10^5$ sec$^{-1}$ IU$^{-1}$. It has been found that the above-described assay procedure allows detection of β-lactamases in the range from $10^{-3}$ to $10^{-5}$ IU/ml.

EXPERIMENTAL

The following examples are offered by way of illustration and not by way of limitation.

All percents and parts not otherwise indicated are by weight, except for mixtures of liquids which are by volume. When a solvent is not indicated, water is intended. All temperatures not otherwise indicated are centigrade. The following abbreviations are employed:

BGG: bovine gamma-globulin; BSA: bovine serum albumin; DMF: N,N-dimethylformamide; DTE: dithioerythritol; ECDI: N,N'-(3'-dimethylaminopropyl)ethyl carbodiimide; EDTA: ethylenediaminetetraacetic acid; G6P: glucose-6-phosphate; G6PDH: glucose-6-phosphate dehydrogenase; HSA: human serum albumin; GO: glucose oxidase; HRP: horseradish peroxidase; Ig: immunoglobulin; NHS: N-hydroxy succinimide; NMR: nuclear magnetic resonance; PBS: phosphate buffered saline (0.1M Na$_2$HPO$_4$, 0.2M NaCl, pH7.0); PEG 6000: polyethylene glycol 6000; THF: tetrahydrofuran; BAG: bromoacetylglycine; AA-PEN- intends intact penicillin linked to a protein; CLA-Pen intends the open lactam ring of penicilloic acid.

1. Preparation of Methyldithioacetic Acid N-Hydroxy Succinimide Ester and Bromoacetylglycine N-Hydroxy Succinimide Ester Methyl dithioacetic acid (0.22 mmol, 30 mg), NHS (0.22 mmol, 25 mg), dicyclohexyl carbodiimide (0.22 mmol, 46 mg), and 3 ml of dry DMF were mixed at 0° C. and stored at 4° C. under argon overnight. The resulting solution is stored in the freezer for subsequent use.

Bromoacetylglycine (0.1 mmol, 38 mg), NHS (0.2 mmol, 22 mg), and ECDI (0.2 mmol, 38 mg) were dissolved in 1 ml of anhydrous DMF in an ice bath under argon. The capped mixture was stirred in a cold room overnight. The tan colored solution was stored in the freezer ready for use.

2. Preparation of N-Methyldithioacetyl Ampicillin by Acylation of Ampicillin with Methyldithioacetic Acid NHS Ester To a slurry of ampicillin (5.24 gm, 13 mmol) in acetone (75 ml) cooled in an ice bath, was slowly added 90 ml of 4% $KHCO_3$. The ampicillin dissolved after a few minutes. A solution of methyldithioacetic acid N-hydroxy succinimide ester (3 gm, 13.1 mmol) in 15 ml of DMF was added to the above ampicillin solution dropwise over 20 minutes. The reaction mixture was stirred in the ice bath for two hours and then most of the acetone was removed by Rotovap under aspirator vacuum. The aqueous solution was extracted with 50 ml of petroleum ether and the organic layer discarded. The aqueous layer was then cooled in an ice bath and acidified to pH2 with 10% $H_3PO_4$. Some solid which separated was dissolved in acetone (3 ml), added to 350 ml of ether, and the aqueous layer was then extracted with the ether. The ethereal layer was washed once with water (50 ml), twice with brine (50 ml) and dried ($MgSO_4$), and then concentrated until an oil separated. The ethereal solution was separated from the oil. Concentration of the ethereal solution yielded 3.75 gm of crude product. The oil was pump dried to give 700 mg of pure product (mp100° C.).

3. Activation of N-Methyldithioacetyl Ampicillin

The N-methyldithioacetyl ampicillin (0.3 mmol) prepared in Experiment 2 and DTE (0.3 mmol) were dissolved in 5 ml of methanol presaturated with argon and 0.5 ml of triethylamine in an ice bath. The mixture was capped and stirred in the cold room overnight. The reaction mixture was concentrated to dryness on a Rotovap and fresh methanol was added (three times). The activated hapten was then taken up in 3.5 ml of argon saturated DMF and used immediately.

4. Activation of BSA and BGG with Bromoacetylglycine NHS Ester

BSA (644 mg) was dissolved in 0.1M argon saturated borate buffer (32 ml) at pH8.5 in an ice bath. Bromoacetylglycine N-hydroxy succinimide ester (BAG-NHS, 293 mg) in DMF was added over 45 minutes and the mixture was allowed to react another 15 minutes. The pH was kept at 8 with 0.1N NaOH added during the course of the addition, but the final pH usually fell to about 7.2. The labeled protein solution was adjusted to pH6.8 before it was purified on a Sephadex®G-50 column. Final volume was 150 ml. The activated BSA was designated BAG-NHS-BSA.

BGG (600 mg) in 0.1M borate buffer (30 ml) was reacted with BAG-NHS (145 mg) in the same manner to yield BAG-NHS-BGG.

5. Preparation of AA-Pen-BSA Conjugate

BAG-NHS-BSA as prepared in Ex. 4 was adjusted to pH7.5 and cooled in an ice bath. Activated ampicillin (282 mg, pH7) as prepared in Ex. 3 was added dropwise to the BAG-NHS-BSA solution. The pH of the final conjunction mixture was adjusted to 7.5, and the mixture was stirred in a cold room for 2 days. The resulting conjugate was concentrated on a Sephadex®G-50 column. The protein fractions were pooled and lyophilized, yielding 600 mg of BSA conjugate. The hapten number was estimated to be 12.

6. Preparation of Antisera to AA-Pen-BSA

Sheep were injected monthly. The first injection contained 1 mg of AA-Pen-BSA conjugate from Ex. 5 emulsified in 0.15M NaCl (1 ml) and complete Freund's adjuvant (1 ml). All subsequent injections contained 1 mg of the conjugate emulsified in 0.15M NaCl (1 ml) and incomplete Freund's adjuvant (1 ml). The sheep were bled monthly, one week after each booster.

7. Preparation of Anti-AA-Pen-BSA Affinity Support to Purify CLA-Pen-BSA Conjugate AA-Pen-BSA antisera from Ex. 6 was used to prepare an affinity support to purify the CLA-Pen-BSA conjugate prepared in Ex. 8. First, the AA-Pen-BSA antisera was treated to remove any anti-BSA activity present. BSA-Sepharose®4B was prepared from CNBr Sepharose®(Pharmacia) and BSA using procedures outlined in the Pharmacia booklet "Affinity Chromatography-Principle and Methods." AA-Pen-BSA antisera (8 ml) was treated with 8 ml of saturated $(NH_4)_2SO_4$ (pH6) to precipitate the immunoglobulin (Ig) fraction. Th precipitate was collected by centrifugation (30 minutes at $10^4$ RPM at 4° C.) and resuspended in 0.1M $NaHCO_3$-0.5M NaCl (pH8.3). It was then dialyzed against the same buffer.

The BSA-Sepharose®4B was used to prepare a 1.5×6.7 cm column. The dialyzed Ig fraction was passed through the BSA-Sepharose®4B column, and Ouchterlony double immunodiffusion confirmed that the anti-BSA activity which had been present in the Ig before chromatography was no longer preset after chromatography.

The absorbed Ig fraction was then coupled to CNBr Sepharose® in the same manner to prepare the anti-AA-Pen-BSA affinity support which is used to absorb conjugate with unopened β-lactam.

8. Preparation of CLA-Pen-BSA Conjugate by Alkaline Hydrolysis of AA-Pen-BSA

AA-Pen-BSA conjugate (100 mg) prepared in Ex. 5 was dissolved in 0.1M borate buffer (pH10) and left overnight at room temperature. The material was then passed over the anti-AA-Pen-BSA affinity support prepared in Ex. 7. The breakthrough peak was collected, pooled, and dialyzed against deionized water. The absence of unhydrolyzed product was confirmed by Ouchterlony immunodiffusion. The conjugate was lyophilized, and the yield was 89.7 mg.

9. Preparation and Testing of Antisera to CLA-Pen-BSA

Sheep were injected monthly. The first injection contained 2 mg of purified CLA-Pen-BSA conjugate from Ex. 8 emulsified in 0.15M NaCl (1 ml) and complete Freund's adjuvant (1 ml). All subsequent injections contained 1 mg of the conjugate emulsified in 0.15M NaCl (1 ml) and incomplete Freund's adjuvant (1 ml). The sheep were bled monthly, one week after each booster. The antisera were titered, and the cross-reactivity to various penicillin derivatives was determined in an RIA.

The RIA was performed as follows. One hundred $\mu$l of antiserum (or antiserum diluted in non-immune sheep serum) was incubated overnight at 4° C. with 25 $\mu$l of $^{14}$C-penicilloic acid. The tracer antigen concentration was 2.5 $\mu$g/ml in PBS (pH7.2). The bound antigen was precipitated by adding 375 $\mu$l of 20% PEG 6000 in PBS (pH7.2) followed by a 30 minute incubation at 4° C. The solution was centrifuged at 4° C. (3000 RPM for 30 minutes) and 350 $\mu$l of the supernatant was removed and counted in a scintillation counter. For antisera from one sheep, it was found that 2 $\mu$l of antiserum was required to precipitate 50% of the tracer.

For cross-reactivity studies, antiserum was reacted with $^{14}$C-penicilloic acid in an amount which, when diluted in 75 $\mu$l of non-immune serum, would precipitate about 50% of the tracer antigen. The diluted antiserum was incubated for 5 hours at 4° C. with increasing concentrations of unlabelled antigens in 25 $\mu$l of PBS. The amount of bound, labeled antigen was determined by the RIA above. It was found for antiserum from one sheep that about 0.45 $\mu$g/ml of penicilloic acid led to a 50% displacement of the tracer, while 31.6 $\mu$g/ml of benzylpenicillin was required to bring about the same displacement.

10. Preparation of Solid Supports

Whatman #2 filter paper disks (15 cm diameter) were activated in 0.1M carbonyl diimidazole for five hours at room temperature. The disks were then washed with water extensively and dried in THF.

CLA-Pen-BSA antisera, as prepared in Ex. 9, was precipitated with (NH$_4$)$_2$SO$_4$ and then dialyzed. The dialyzed antisera (250 mg/$\mu$l) and GO (100 $\mu$/ml) were added to PBS (pH7.0). The resulting solution was reacted with the activated disks (20 ml/disk) for four hours. After washing extensively with PBS, the disks were saturated with a stabilizer (2 mg/ml BSA and 15% sucrose in PBS) and then lyophilized. The disks were then cut into ~0.25 in. pads and mounted on plastic strips (referred to as "dipsticks") for use in the assays described hereinafter.

11. Conjugation of HRP to Ampicilloic Acid

Ampicilloic acid was prepared in the following manner. Ampicillin trihydrate (10 gm, Sigma) was suspended in 50 ml of water and dissolved by the addition of 10N NaOH. The pH was maintained at 12 by the addition of 10N NaOH. After 1 hour, the pH was adjusted to 7.0 with 6N HCl. 2-Propanol (140 ml) was then added, and the solution allowed to stand for 4 hours at 4° C., after which time crystals had formed. The crystals were filtered and washed several times with cold 2-propanol:water (3:1) and allowed to dry at room temperature. Thin layer chromatography confirmed that this material was essentially all ampicilloic acid. Yield was 1.97 gm.

The ampicilloic acid was conjugated to HRP as follows. HRP powder (60 mg) was dissolved in 5 ml water. The actual protein concentration was determined to be 8.8 mg/ml, indicating that only 73% of the powder was actually HRP. The HRP solution was dialyzed overnight against several changes of distilled water. The dialyzed solution (4.2 ml, 8.3 mg/ml) was reacted with 0.8 ml of 0.1M NaIO$_4$ for 60 minutes at room temperature. The reaction mixture was then passed through a Sephadex ®G-25 column equilibrated with 5 mM sodium acetate buffer (pH4.6), and the peak was collected by visual inspection. To 4.5 ml of the purified HRP (3.9 mg/ml) was added 32 mg of the prepared ampicilloic acid in 0.5 ml of 2M Na$_3$PO$_4$ (pH7). The mixture was stirred at 4° C. for 30 minutes, after which 0.6 ml of a 10 mg/ml solution of NaBH$_3$CN was added. The conjugate was purified on a Sephadex ®G-25 column equilibrated with water. The conjugate was dialyzed against PBS.

12. Assays

Cross-reactivity between benzylpenicillin, ampicillin, penicilloic acid and ampicilloic acid was determined as follows. Dipsticks as prepared in Ex. 10 were incubated in serial dilutions of each of the haptens dissolved in PBS (pH7.2). The dipsticks were then blotted and transferred to solution of the ampicilloic acid-HRP conjugate (Ex. 11, 200 ng/ml) in PBS having 0.2% BSA and allowed to incubate for 15 minutes at room temperature. The dipsticks were then removed, blotted, and transferred to a solution consisting of 0.2% BSA, 0.05M $\beta$-D-glucose, and 4-Cl-1-naphthol (300 ng/ml) in PBS. After a 15 minute incubation in this solution, the dipsticks were removed, blotted, and a color difference unit (CDU) reflectance value (relative to a blank pad incubated in developer (CDU$_o$) was determined on a Macbeth Reflectance Spectrometer. The results are set forth in Table 1.

TABLE 1

| Antigen Conc. (ng/ml) | CDU/CDU$_o$ | | | |
|---|---|---|---|---|
| | Benzyl-penicillin | Ampicillin | Penicilloic Acid | Ampicilloic Acid |
| 0 | 1 | 1 | 1 | 1 |
| 10$^{-1}$ | 0.99 | 1.05 | 1.05 | 1.02 |
| 10$^0$ | 0.98 | 1.09 | 1.09 | 0.98 |
| 10$^1$ | 0.91 | 1.00 | 0.77 | 0.85 |
| 10$^2$ | 0.96 | 1.01 | 0.50 | 0.64 |
| 10$^3$ | 0.90 | 0.96 | 0.35 | 0.45 |
| 10$^4$ | 0.72 | 0.54 | 0.18 | 0.34 |
| 10$^5$ | 0.67 | 0.23 | — | — |

These results indicate that the anti-CLA-Pen-BSA is much more reactive with compounds having the open $\beta$-lactam ring (i.e., benzylpenicilloic and ampicilloic acid) than the corresponding compounds having closed $\beta$-lactam rings (i.e., benzylpenicillin and ampicillin) at hapten concentrations ranging from about 10 to 10,000 ng/ml.

A standard curve for the assay of $\beta$-lactamase was developed as follows. Serial dilutions of $\beta$-lactamase in normal human serum were prepared. Samples (100 $\mu$l) of varying concentration were incubated with 900 $\mu$l of a substrate solution consisting of 11.1 $\mu$g/ml of benzylpenicillin in PBS (pH7.2), for 1 hour at 37° C. After incubation, the samples were rapidly brought to room temperature, and the dipstick assay described above was carried out, with the first incubation being the dipstick in the enzyme reaction mixture. The results are set forth in Table 2.

TABLE 2

| $\beta$-Lactamase Concentration (IU/ml) | CDU |
|---|---|
| 0 | 14.7 |
| $10^{-5}$ | 14.5 |
| $10^{-4}$ | 13.2 |
| $10^{-3}$ | 9.3 |
| $10^{-2}$ | 6.0 |
| $10^{-1}$ | 5.2 |
| $10^{0}$ | 4.6 |
| $10^{1}$ | 5.0 |
| $10^{2}$ | 5.2 |

A precision study was done where a single human serum sample, spiked to different levels with $\beta$-lactamase, was assayed at each level fifteen times. Each sample (100 $\mu$l) was incubated with the substrate solution described above for one hour at 37° C. After bringing the samples to room temperature, they were assayed using the dipstick procedure. The results were read from the standard curve and are presented in Table 3.

TABLE 3

| Enzyme Activity IU/ml | CDU$^a$ | S.D. | % C.V. |
|---|---|---|---|
| 0 | 20.38 | 2.14 | 10.5 |
| $10^{-5}$ | 20.65 | 2.34 | 11.3 |
| $10^{-4}$ | 17.60 | 1.35 | 7.7 |
| $10^{-3}$ | 14.31 | 1.04 | 7.3 |
| $10^{-2}$ | 7.91 | 0.69 | 7.7 |

$^a$Mean from 15 replications.

A variation study was undertaken with 20 serum samples. These were from individuals who had no known bacterial infection, but they varied markedly in their physical state, with some being clear, others being hemolyzed, and still others being very lipemic and turbid. The sera was spiked with varying levels of $\beta$-lactamase. The assay was performed as previously described. The results of this study are presented in Table 4.

TABLE 4

| Enzyme Activity IU/ml | CDU$^a$ | S.D. | % C.V. |
|---|---|---|---|
| 0 | 23.80 | 0.99 | 4.16 |
| $10^{-5}$ | 20.91 | 1.66 | 7.90 |
| $10^{-4}$ | 20.65 | 1.45 | 7.00 |
| $10^{-3}$ | 12.06 | 0.85 | 7.00 |
| $10^{-2}$ | 8.68 | 0.96 | 11.10 |

$^a$Mean from 20 serum samples.

Three assay protocols were compared. Each protocol employed the following reagents:
Enzyme conjugate reagent: 200 ng/ml HRP-ampicilloic acid (Ex. 11) and 2 mg/ml BSA in PBS.
GO-HRP substrate solution: 9 mg/ml glucose, 300 $\mu$g/ml 4-Cl-1-naphthol, 1 mg/ml BSA in PBS.
Penicillin solution: 11.1 $\mu$g/ml benzylpenicillin and $10^{-3}$M EDTA in PBS.

For protocol (A), sample (100 $\mu$l) is incubated for one hour at 37° C. with penicillin solution (900 $\mu$l). A dipstick is immersed in the solution for 30 minutes at room temperature, after which time it is washed and transferred to the enzyme conjugate reagent for 15 minutes. After washing, the dipstick is immersed in the GO-HRP substrate solution for 15 minutes and, after blotting, is read on a suitable reflectometer.

For protocol (B), sample (100 $\mu$l) and penicillin solution (900 $\mu$l) are combined and the dipstick immediately immersed for one hour at 37° C. The dipstick is washed and transferred to enzyme conjugate reagent for 15 minutes, after which time it is washed and transferred to the GO-HRP substrate solution for 15 minutes. After blotting, the dipstick is read on a suitable reflectometer.

For protocol (C), sample (100 $\mu$l) was incubated for 30 minutes at room temperature in a tube coated with benzylpenicillin (10 $\mu$g) vacuum-dried from methanol. Enzyme conjugate reagent (900 $\mu$l) was then added to the tube and the dipstick immersed for 15 minutes. After washing, the dipstick is transferred to the GO-HRP substrate solution for 15 minutes, and, after blotting, read on a suitable reflectometer.

Serial dilutions of $\beta$-lactamase in normal human serum were prepared. Each of the above assays were performed, and the results are set forth in Table 5.

TABLE 5

| Enzyme Activity IU/ml | Protocol (CDU/CDU$_o$) | | |
|---|---|---|---|
| | A | B | C |
| 0 | 1.00 | 1.00 | 1.00 |
| $10^{-5}$ | 1.00 | 1.00 | 1.00 |
| $10^{-4}$ | 1.00 | 0.72 | 0.86 |
| $10^{-3}$ | 0.42 | 0.47 | 0.76 |
| $10^{-2}$ | 0.30 | 0.31 | 0.49 |
| $10^{-1}$ | 0.22 | 0.23 | 0.43 |

Both assay protocols B and C provide a suitable standard curve for measuring the level of $\beta$-lactamase in the range from about $10^{-1}$ to $10^{-4}$ IU/ml.

The compositions of the subject invention provide for reagents which allow a sensitive and accurate assay for penicilloic acids in patient serum samples. The antigenic conjugates provide for the efficient production of antibodies having high affinity and high titer for penicilloic acid. The combination of these antibodies and the enzyme conjugates provides for an accurate, rapid assay for penicilloic acid. By adding a preselected amount of penicillin to the serum sample, an assay for $\beta$-lactamases can be performed where the $\beta$-lactamase level is inferred from the amount of penicilloic acid produced in a given time period.

Although the foregoing invention has been described in some detail by way of illustration and example for purposes of clarity and understanding, it will be obvious that certain changes and modifications may be practiced within the scope of the appended claims.

What is claimed is:

1. A compound of the formula:

$$\left[ \begin{array}{c} H_3C \\ H_3C \end{array} \mathrm{X} \begin{array}{c} S \\ \\ \end{array} \begin{array}{c} \\ NH^{CO_2H} \\ CO_2X \end{array} CH-NH-\overset{O}{\underset{\|}{C}}-\overset{Y}{\underset{|}{CH}}-NH-R \right]_n -Z$$

wherein:
X is an alkali metal or hydrogen;
Y is an organic radical of naturally occurring or synthetic penicillin antibiotics;
R is a linking group having from 3 to 9 carbon atoms and from 0 to 5 heteroatoms;

Z is a poly(amino acid) which is an antigen or an enzyme; and n is from 1 to the molecular weight of Z divided by 500.

2. A compound as in claim 1, wherein R is a straight chain having from 5 to 12 atoms in the chain.

3. A compound as in claim 2, where R is:

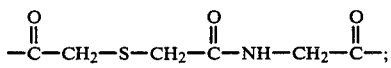

4. A compound as in claim 1, wherein Y is phenyl.
5. A compound as in claim 1, wherein Z is an antigen.
6. A compound as in claim 1, wherein Z is a bovine serum albumin or bovine gamma-globulin.
7. A compound as in claim 1, wherein Z is an enzyme.
8. A compound as in claim 1, wherein Z is horseradish peroxidase.

9. A method for determining the presence of or amount of a penicilloic acid in a sample which comprises:

combining in an assay medium a sample suspected of containing a penicilloic acid, enzyme-penicilloic acid conjugate and a solid support to which antibodies to said penicilloic acid are bound wherein said antibodies are obtained in response to an immunogen and wherein said immunogen and said enzyme-penicilloic acid conjugate are compounds according to claim 1, whereby said conjugate binds to said antibodies in inverse proportion to the amount of said penicilloic acid in said sample;

separating said support from said assay medium; and determining the enzyme activity on said support or in said assay medium as an indication of the presence of or the amount of said penicilloic acid in said sample.

10. A method for determining the presence of or amount of a penicilloic acid in a sample which comprises:

combining in an assay medium a sample suspected of containing a penicilloic acid, enzyme-penicilloic acid conjugate and a solid support to which antibodies are bound wherein said antibodies are obtained in response to an antigen according to claim 6, and wherein said enzyme-penicilloic acid conjugate is a compound of the formula:

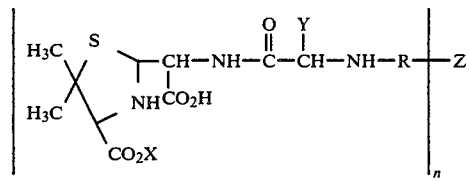

wherein:
X is an alkali metal or hydrogen;
Y is an organic radical of naturally occurring or synthetic penicillin antibiotics;
R is a linking group having from 3 to 9 carbon atoms and from 0 to 5 heteroatoms;
Z is a poly(amino acid) which is an enzyme; and
n is from 1 to the molecular weight of Z divided by 500, whereby said conjugate binds to said antibodies in inverse proportion to the amount of said penicilloic acid in said sample;

separating said support from said assay medium; and determining the enzyme activity on said support or in said assay medium as in indication of the presence of or the amount of said penicilloic acid in said sample.

11. A method for determining the presence of or amount of a penicilloic acid in a sample which comprises:

combining in an assay medium, a sample suspected of containing a penicilloic acid, antibodies to said penicilloic acid, wherein said antibodies are obtained in response to an immunogen, and said penicilloic acid conjugated to an enzyme, wherein said immunogen and said enzyme-penicilloic acid conjugate are compounds according to claim 1, under conditions where said penicilloic acid conjugate can be distinguished between being bound to antibodies and being unbound, the amount bound being an indication of the amount of penicilloic acid in said sample; and determining either the amount of bound or unbound conjugate as an indication of the amount of penicilloic acid in said sample.

12. A method according to claim 11, wherein said sample is formed by combining a sample suspected of having β-lactamase with a penicillin precursor to said penicilloic acid.

13. A method according to claim 11, wherein said enzyme is horse radish peroxidase.

* * * * *